United States Patent [19]

Schonbeck et al.

[11] 3,932,405
[45] Jan. 13, 1976

[54] PHENYLPYRIDAZINES

[75] Inventors: Rupert Schonbeck, Leonding near Linz; Engelbert Kloimstein, Eferding; Hubert Mayr, Leonding near Linz; Alfred Diskus; Engelbert Auer, both of Linz, all of Austria

[73] Assignee: Chemie Linz Aktiengesellschaft, Linz, Austria

[22] Filed: Nov. 14, 1973

[21] Appl. No.: 415,555

[30] Foreign Application Priority Data
Nov. 16, 1972  Germany.............................. 2256172

[52] U.S. Cl................................. 260/250 A; 71/92
[51] Int. Cl.²..................................... C07D 237/10
[58] Field of Search ............................... 260/250 A

[56] References Cited
UNITED STATES PATENTS
3,790,571  2/1974  Diskus et al..................... 260/250 A
FOREIGN PATENTS OR APPLICATIONS
2,129,109  1/1973  Germany ....................... 260/250 A

*Primary Examiner*—Donald G. Daus
*Assistant Examiner*—Anne Marie T. Tighe
*Attorney, Agent, or Firm*—Wenderoth, Lind & Ponack

[57] ABSTRACT

Phenylpyridazine compounds of the general formula

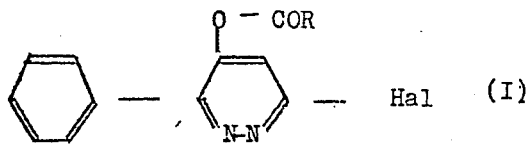

in which Hal is a chlorine or bromine atom and R is a straight-chain or branched alkyl group containing 2 to 20 carbon atoms when Hal is chlorine and 1 to 20 carbon atoms when Hal is bromine, or is the group —OR′, wherein R′ is an alkyl group of 1 to 18 carbon atoms which may be straight-chain or branched, and which have valuable herbicidal properties.

30 Claims, No Drawings

PHENYLPYRIDAZINES

This invention relates to phenylpyridazine compounds, a process for the preparation thereof and herbicidal compositions containing them.

It has been known for a considerable time that pyridazine derivatives influence plant growth. Thus, pyridazines which contain two or three halogen atoms or up to two halogen atoms and, in addition, alkylated amino groups, alkoxy groups or alkylmercapto groups, are described in Austrain Pat. No. 198,997 as agents for influencing plant growth. The compounds described in detail therein are either total herbicides or have other effects on the plant such as, for example, defoliation. Furthermore, 3-chloro-pyridazine-6-oxyacetic acid may be used as a hormonal agent for combating weeds but the breadth of its activity is inadequate.

West German Nos. 1,567,131 and 1,910,620 disclose phenylpyridazine ethers which may be used to combat grasses in rice cultures.

It has now been found that previously unknown phenylpyridazine derivatives of the general formula:

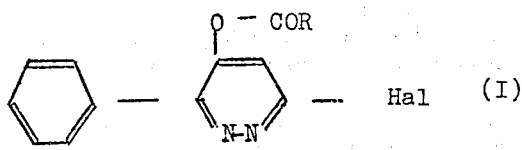

in which Hal is a chlorine or bromine atom and R is a straight-chain or branched alkyl group containing 2 to 20 carbon atoms when Hal is chlorine or 1 to 20 carbon atoms when Hal is bromine, or is the group —OR', wherein R' is an alkyl group containing 1 to 18 carbon atoms which may be straight-chain or branched, display very advantageous herbicidal properties and furthermore are tolerated by numerous crop plants, for example cerals.

The present invention also provides a process for the preparation of a 3-phenyl-6-halopyridazine compound of the formula (I) which comprises reacting 3-phenyl-6-chloro-4-hydroxypyridazine or 3-phenyl-6-bromo-4-hydroxypyridazine or a salt thereof, at an elevated temperature, optionally in the presence of a solvent and optionally with the addition of an acid acceptor, with an acid chloride of the formula Cl — COR, wherein R is as defined above, or an acid anhydride of the formula R"OCOCOR", wherein R" is a straight-chain or branched alkyl group containing 1 to 20 carbon atoms.

The addition of an acid acceptor, for example of a tertiary amine, if the reaction is to be carried out with an acid chloride, accelerates the reaction and allows it to be performed even at normal temperature.

The reaction of the initial pyridazine compound with the acid chloride should be carried out at a temperature above 100°C, especially if an acid acceptor is not added. Under these conditions, hydrochloric acid gas is split off spontaneously and the desired reaction takes place largely quantitatively. Since the phenyl-halohydroxypyridazine is sparingly soluble and high-melting, in some cases, it may be of advantage to use a salt of the acid pyridazine compound, for example an amine salt, and a suitable inert solvent.

If instead of the acid chloride the corresponding acid anhydride is employed, the yield is generally less since the reaction leads to an equilibrium condition because the carboxylic acid liberated again partially splits the ester.

3-Phenyl-4-hydroxy-6-chloropyridazine of melting point 220°C. (decomposition) which is used as the starting material may be obtained from 3-phenyl-4,6-dichloropyridazine by heating with sodium hydroxide solution.

Equally, 3-phenyl-4-hydroxy-6-bromopyridazine, melting point 215°C (decomposition) may be obtained by reacting 3-phenyl-4,6-dibromopyridazine with sodium hydroxide solution at boiling point.

The esters according to the invention, of the formula (I), are mostly viscous liquids of high boiling point which cannot be distilled without decomposition.

They may be decomposed by water relatively easily and then give on the one hand the initial pyridazine which, because of its low solubility, precipitates directly as a solid from the ester and, on the other hand, the corresponding acid.

The invention further provides a herbicidal composition for the selective combating of weeds in crop plants which comprises, as the active ingredient, one or more compounds of the formula (I) in admixture with solid and/or liquid inert extenders or diluents and/or wetting agents.

Since the compounds are not active in the sense of growth substances, the danger of damage to adjoining crops is substantially less. The substances are therefore also preferentially suitable for combating weeds in monocotyledon crop plants in the immediate vicinity of sensitive crops.

The compositions according to the invention may be in the form of dispersions or emulsions, pulverulent preparations of granules. They also may be admixed with other herbicidal active substances.

The possibility of combination with various growth regulators such as, for example, 2-chloroethyl-trimethylammonium chloride (Chlormequat) is of great practical importance.

Conjoint application of the compounds according to the invention with fungicides, insecticides, other biocides and/or plant nutrients is also of advantage.

For compositions in the form of aqueous dispersions or emulsions it is advisable to add a dispersing agent such as, for example, sodium oleyl-methyl-tauride. Solid extenders which may be used include various types of clays, for example kaolin.

The combination of the compounds according to the invention with a non-phytotoxic oil, for example a mineral oil-emulsifier mixture, consisting of a paraffin mineral oil and an emulsifier, is advantageous. The herbicidal action may be increased yet further by the addition of such a "spray oil" to a spraying solution of the compound according to the invention. Such combinations usually contain 0.1 to 10 kg of the active compound according to the present invention and 1 to 10 liters of a non-phytotoxic oil, distributed in an amount of water of 50 to 1,000 liters.

The preparation and mode of action of the compounds according to the invention will be illustrated in more detail in the Examples which follow:

EXAMPLE 1

5.0 G of 3-phenyl-4-hydroxy-6-chloropyridazine were boiled with 20 g. of propionic acid chloride for 3 hours under a reflux condenser. The excess propionic acid chloride was distilled off in vacuo, the oily residue was stirred with 50 ml. of petroleum ether and filtered using active charcoal and the filtrate was evaporated. A light yellow oil remained. $n_D^{20} = 1.5828$.

Yield: 4.6 g, corresponding to 75% of theory, of 3-phenyl-6-chloro-pyridazinyl-(4)-propionic acid ester.

| C calculated | 59.44% | H calculated | 4.22 % | N calculated | 10.67% |
|---|---|---|---|---|---|
| found | 58.9% | found | 4.3% | found | 10.3% |
| Cl calculated | 13.50% | O calculated | 12.18% | | |
| found | 13.2% | found | 12.5% | | |

The following compounds were prepared in an analogous manner:
a. 3-Phenyl-6-chloro-pyridazinyl-(4)-n-butyric acid ester; 60% yield; $n_D^{20} = 1.5765$;
b. 3-Phenyl-6-chloro-pyridazinyl-(4)-isobutyric acid ester; 90% yield; $n_D^{20} = 1.5696$;
c. 3-Phenyl-6-chloro-pyridazinyl-(4)-n-valeric acid ester; 88% yield; $n_D^{20} = 1.5628$;
d. 3-Phenyl-6-chloro-pyridazinyl-(4)-isovaleric acid ester; 78% yield; $n_D^{20} = 1.5595$;
e. 3-Phenyl-6-chloro-pyridazinyl-(4)-2'-ethylhexanoic acid ester; 65% yield; $n_D^{20} = 1.5355$;
f. 3-Phenyl-6-chloro-pyridazinyl-(4)-caprylic acid ester; 65% yield; $n_D^{20} = 1.5265$.

EXAMPLE 2

5.0 G of 3-phenyl-4-hydroxy-6-chloropyridazine were suspended in 50 ml of benzene, 2.75 g of triethylamine were added and the mixture was stirred. A solution of 8.0 g of stearic acid chloride in 20 ml of benzene was added to the vigorously stirred mixture of the resulting salt with benzene. Whilst doing so, the temperature of the mixture rose from 22°C to 40°C. The reaction was allowed to take place for 15 minutes whilst stirring, 20 ml of water were then added, the mixture was stirred briefly, the aqueous phase was separated off, the benzene solution was dried with $Na_2SO_4$ and filtered using active charcoal, and the filtrate was evaporated. A viscous oil was left, which solidified after some hours. Recrystallisation from petroleum ether gave crystals of melting point 62°–64°C. Yield: 10.0 g corresponding to 87% of theory of 3-phenyl-6-chloropyridazinyl-(4)-stearic acid ester.

| C calculated | 71.08% | H calculated | 8.74% | N calculated | 5.92% |
|---|---|---|---|---|---|
| found | 71.2% | found | 8.7% | found | 5.8% |
| Cl calculated | 7.49% | O calculated | 6.76% | | |
| found | 7.4% | found | 6.8% | | |

The following compounds were prepared analogously:
a. 3-Phenyl-6-chloro-pyridazinyl-(4)-pivalic acid ester; 65% yield; $n_D^{20} = 1.5462$;
b. 3-Phenyl-6-chloro-pyridazinyl-(4)-n-caproic acid ester; 54% yield; $n_D^{20} = 1.5380$;
c. 3-Phenyl-6-chloro-pyridazinyl-(4)-oenanthic acid ester; 62% yield; $n_D^{20} = 1.5465$;
d. 3-Phenyl-6-chloro-pyridazinyl-(4)-pelargonic acid ester; 58% yield; melting point=18°–22°C;
e. 3-Phenyl-6-chloro-pyridazinyl-(4)-myristic acid ester; 75% yield; melting point=52°–54°C;
f. 3-Phenyl-6-bromopyridazinyl-(4)-n-butyric acid ester; 85% yield; $n_D^{20} = 1.5783$;
g. 3-Phenyl-6-bromopyridazinyl-(4)-n-octanoic acid ester; 86% yield; $n_D^{20} = 1.5548$.

EXAMPLE 3

5.0 G of 3-phenyl-4-hydroxy-6-chloropyridazine were mixed with 20 g of chloroformic acid n-pentyl ester and heated to 130°–140°C for 1 hour. The excess chloroformic acid ester was then distilled off in vacuo, the oily residue which remained was stirred with 50 ml of petroleum ether and filtered using active charcoal and the filtrate was evaporated in vacuo. A light yellow oil remained.
$n_D^{20} = 1.5570$ Yield: 5.9 g, corresponding to 76% of theory, of 3-phenyl-6-chloro-pyridazinyl-(4)-n-pentyl carbonate.

| C calculated | 59.91% | H calculated | 5.34% | N calculated | 8.73% |
|---|---|---|---|---|---|
| found | 59.8% | found | 5.5% | found | 8.6% |
| Cl calculated | 11.05% | O calculated | 14.96% | | |
| found | 11.6% | found | 14.6% | | |

The following compounds were prepared analogously:
a. 3-Phenyl-6-chloro-pyridazinyl-(4)-ethyl carbonate; 54% yield; $n_D^{20} = 1.5825$;
b. 3-Phenyl-6-chloro-pyridazinyl-(4)-isopropyl carbonate; 52% yield; $n_D^{20} = 1.5602$;
c. 3-Phenyl-6-chloro-pyridazinyl-(4)-isobutylcarrbonate; 46% yield; $n_D^{20} = 1.5630$.

EXAMPLE 4

5.0 G of 3-phenyl-4-hydroxy-6-chloropyridazine were suspended in 70 g of benzene, a solution of 0.90 g of NaOH in 5 ml of water was added and the water was removed through a water separator by boiling under reflux, with vigorous stirring. 3.5 G of chloroformic acid n-hexyl ester were added to the mixture thus obtained, which consisted of the sodium salt of 3-phenyl-4-hydroxy-6-chloropyridazine and benzene, and the whole was boiled for 30 minutes under reflux. It was then cooled and briefly stirred with 10 ml of water, the aqueous phase was separated off, the benzene solution was dried with $Na_2SO_4$ and filtered using active charcoal and the filtrate was evaporated. The oily residue was stirred with 50 ml of petroleum ether and filtered using active charcoal, and the filtrate was evaporated in vacuo.

A light yellow oil was left. $n_D^{20} = 1.5380$

Yield: 3.5 g, corresponding to 43% of theory, of 3-phenyl-6-chloro-pyridazinyl-(4)-n-hexyl carbonate.

| | | | | | | |
|---|---|---|---|---|---|---|
| C calculated | 60.98% | H calculated | 5.72% | N calculated | 8.37% | |
| found | 60.7% | found | 5.8% | found | 8.4% | |
| Cl calculated | 10.59% | O calculated | 14.3% | | | |
| found | 10.4% | found | 14.7% | | | |

EXAMPLE 5

10 g of 3-phenyl-4-hydroxy-6-chloropyridazine were suspended in 100 ml of benzene, 5.5 g of triethylamine were added, the mixture was stirred for 5 minutes, a solution of 9.4 g of chloroformic acid 2-ethylhexyl ester was then added rapidly and the mixture was allowed to react for 15 minutes. It was then briefly stirred with 20 ml of water, the aqueous phase was separated off, the benzene solution was dried with $Na_2SO_4$ and filtered using active charcoal and the filtrate was evaporated in vacuo. The oil which was left as a residue was stirred with 100 ml of petroleum ether and filtered using active charcoal, and the filtrate was again evaporated in vacuo.

A light yellow oil was obtained. $n_D^{20} = 1.5375$

Yield: 12.8 g, corresponding to 73% of theory, of 3-phenyl-6-chloro-pyridazinyl-(4)-2'-ethylhexyl carbonate.

| | | | | | |
|---|---|---|---|---|---|
| C calculated | 62.89% | H calculated | 6.39% | N calculated | 7.72% |
| found | 62.8% | found | 7.0% | | 7.3% |
| Cl calculated | 9.77% | O calculated | 13.23% | | |
| found | 10.1% | found | 12.7% | | |

The following compounds were prepared analogously:

a. 3-Phenyl-6-chloro-pyridazinyl-(4)-n-propyl carbonate; 77% yield; $n_D^{20} = 1.5570$;
b. 3-Phenyl-6-chloro-pyridazinyl-(4)-n-butyl carbonate; 81% yield; $n_D^{20} = 1.5590$;
c. 3-Phenyl-6-chloro-pyridazinyl-(4)-isoamyl carbonate; 75% yield; $n_D^{20} = 1.5485$;
d. 3-Phenyl-6-chloro-pyridazinyl-(4)-n-heptyl carbonate; 71% yield; $n_D^{20} = 1.5340$;
e. 3-Phenyl-6-chloro-pyridazinyl-(4)-n-octyl carbonate; 78% yield; $n_D^{20} = 1.5340$;
f. 3-Phenyl-6-chloro-pyridazinyl-(4)-n-decyl carbonate; 86% yield; $n_D^{20} = 1.5280$;
g. 3-Phenyl-6-bromo-pyridazinyl-(4)-n-amyl carbonate; 75% yield; $n_D^{20} = 1.5687$.

EXAMPLE 6

20 G of (3-phenyl-6-chloro-pyridazinyl)-(4))-isobutyrate, 70 g of xylene and 10 g of alkylarylsulphonate mixed with polyoxyethylene-sorbitane-tall oil ester were mixed; on stirring the emulsion concentrate, thus obtained, into the amount of water required for application to the plant, a stable emulsion was obtained.

EXAMPLE 7

50 G of (3-phenyl-6-chloro-pyridazinyl-(4))-n-pentyl carbonate, 43 g of xylene and 7 g of alkylarylsulphonate mixed with polyoxyethylene-sorbitane-tall oil ester were mixed. The emulsion concentrate gave a stable emulsion on stirring into water. All further compounds according to the invention were formulated similarly.

EXAMPLE 8

Weeds grown in a greenhouse:

| | |
|---|---|
| Erodium cicutarium | Stork's bill |
| Centaurea jacea | Knapweed |
| Lapsana communis | Nipplewort |
| Galium aparine | Goosegrass |
| Stellaria media | Chickweed |
| Matricaria chamomilla | Camomile |
| Lamium purpureum | Deadnettle |
| Veronica hederaefolia | Speedwell | were sprayed with the spraying solution of the compound according to the invention after the weeds had reached the 4–6 leaf stage. The spraying solution was used in the form of an emulsion concentrate. To prepare an emulsion concentrate, 20% by weight of the active substances were dissolved in 70% by weight of xylene and 10% by weight of an emulsifier (alkylarylsulphonate mixed with polyoxyethylene-sorbitane-tall oil ester) were added. The dosage was between 380 g. and 1,160 g. of the active compound per hectare.

14 Days after the treatment the herbicidal effect on the weeds was determined in accordance with the E.W.R.C. Assessment Scheme. (E.W.R.C. = European Weed Research Council). The numerical values 1 to 9 correspond to the following proportions destroyed

| Rating of the herbicidal action | Corresponding to % destruction of the weeds |
|---|---|
| 1 | 100 |
| 2 | 97.5 |
| 3 | 95 |
| 4 | 90 |
| 5 | 85 |
| 6 | 75 |
| 7 | 65 |
| 8 | 32.5 |
| 9 | 0 |

Example 8

| Formula I | | Herbicidal action on different weeds (ratings 1 – 9) | | | | | | | | |
|---|---|---|---|---|---|---|---|---|---|---|
| R = | al. | Active compound kg/ha | | Erodium cicut. | Centaurea jacea | Lapsana comm. | Galium aparine | Stellaria media | Matricaria Chamom. | Lamium prup | Veronica hed. |
| $C_2H_5$ | Cl | 0.38 | 0.63 | 1/1 | 1/1 | 1/1 | 1/1 | 1/1 | 1/1 | 2/1 | 1/1 |
| $C_3H_7$ | Cl | 0.45 | 0.67 | 1/1 | 3/1 | 1/1 | 2/1 | 4/2 | 2/1 | 1/1 | 1/1 |
| $CH.(CH_3)_2$ | Cl | 0.42 | 0.67 | 1/1 | 1/1 | 1/1 | 1/1 | 1/1 | 1/1 | 1/1 | 1/1 |
| $C_4H_9$ | Cl | 0.42 | 0.70 | 1/1 | 1/1 | 1/1 | 1/1 | 3/2 | 2/1 | 1/1 | 1/1 |
| $CH_2CH.(CH_3)_2$ | Cl | 0.42 | 0.70 | 1/1 | 1/1 | 1/1 | 1/1 | 5/3 | 3/2 | 1/1 | 1/1 |
| $C_7H_{15}$ | Cl | 0.48 | 0.80 | 1/1 | 3/1 | 1/1 | 1/1 | 4/3 | 3/2 | 1/1 | 1/1 |

Example 8-continued

| Formula I R = | Hal. | Active compound kg/ha | | Herbicidal action on different weeds (ratings 1 - 9) | | | | | | | |
|---|---|---|---|---|---|---|---|---|---|---|---|
| | | | | Erodium cicut. | Centaurea jacea | Lapsana comm. | Galium aparine | Stellaria media | Matricaria Chamom. | Lamium prup | Veronica hed. |
| CH.(C$_2$H$_5$).C$_4$H$_9$ | Cl | 0.48 | 0.80 | 1/1 | 3/2 | 1/1 | 1/1 | 5/4 | 4/3 | 1/1 | 1/1 |
| C$_6$H$_{13}$ | Cl | 0.46 | 0.77 | 1/1 | 3/1 | 1/1 | 1/1 | 2/1 | 2/1 | 3/2 | 2/1 |
| C$_8$H$_{17}$ | Cl | 0.50 | 0.84 | 1/1 | 2/1 | 1/1 | 1/1 | 2/1 | 2/1 | 3/1 | 2/1 |
| C$_{13}$H$_{27}$ | Cl | 0.60 | 1.01 | 1/1 | 2/1 | 1/1 | 1/1 | 2/1 | 2/1 | 5/2 | 2/1 |
| C$_{17}$H$_{35}$ | Cl | 0.69 | 1.16 | 1/1 | 5/2 | 2/1 | 5/2 | 2/1 | 2/1 | 5/2 | 5/3 |
| O.C$_2$H$_5$ | Cl | 0.45 | 0.67 | 1/1 | 1/1 | 1/1 | 3/1 | 6/3 | 1/1 | 1/1 | 1/1 |
| O.CH.(CH$_3$)$_2$ | Cl | 0.42 | 0.70 | 1/1 | 1/1 | 1/1 | 1/1 | 6/3 | 1/1 | 1/1 | 1/1 |
| O.C$_4$H$_9$ | Cl | 0.44 | 0.74 | 1/1 | 1/1 | 1/1 | 3/1 | 5/2 | 1/1 | 1/1 | 3/2 |
| O.CH$_2$CH.(CH$_3$)$_2$ | Cl | 0.44 | 0.74 | 1/1 | 1/1 | 1/1 | 3/1 | 4/2 | 1/1 | 1/1 | 1/1 |
| O.C$_5$H$_{11}$ | Cl | 0.46 | 0.77 | 1/1 | 1/1 | 1/1 | 1/1 | 1/1 | 1/1 | 1/1 | 1/1 |
| O.C$_6$H$_{13}$ | Cl | 0.48 | 0.81 | 1/1 | 1/1 | 4/2 | 6/5 | 7/5 | 7/5 | 4/2 | 4/2 |
| O.C$_7$H$_{15}$ | Cl | 0.50 | 0.84 | 1/1 | 1/1 | 1/1 | 1/1 | 3/2 | 1/1 | 4/2 | 4/2 |
| O.C$_8$H$_{17}$ | Cl | 0.52 | 0.88 | 1/1 | 1/1 | 1/1 | 1/1 | 3/1 | 1/1 | 4/1 | 5/2 |
| O.CH$_2$CH(C$_2$H$_5$)C$_4$H$_9$ | Cl | 0.52 | 0.88 | 1/1 | 1/1 | 1/1 | 1/1 | 3/1 | 1/1 | 4/1 | 3/1 |
| O.C$_{10}$H$_{21}$ | Cl | 0.56 | 0.94 | 1/1 | 1/1 | 1/1 | 1/1 | 1/1 | 1/1 | 1/1 | 1/1 |
| C(CH$_3$)$_3$ | Cl | 0.46 | 0.77 | 1/1 | 1/1 | 1/1 | 1/1 | 1/1 | 1/1 | 1/1 | 1/1 |
| O.CH$_2$CH$_2$CH(CH$_3$)$_2$ | Cl | 0.42 | 0.70 | 1/1 | 1/1 | 1/1 | 1/1 | 1/1 | 1/1 | 1/1 | 1/1 |
| C$_3$H$_7$ | Br | 0.40 | 0.67 | 1/1 | 1/1 | 1/1 | 1/1 | 2/1 | 1/1 | 2/1 | 1/1 |
| C$_7$H$_{15}$ | Br | 0.46 | 0.77 | 1/1 | 1/1 | 1/1 | 1/1 | 2/1 | 1/1 | 1/1 | 2/1 |
| O.C$_5$H$_{11}$ | Br | 0.44 | 0.74 | 1/1 | 1/1 | 1/1 | 1/1 | 2/1 | 1/1 | 2/1 | 2/1 |

EXAMPLE 9

Crop plants grown in a greenhouse

| | |
|---|---|
| Triticum vulgare | Wheat |
| Hordeum sativum | Barley |
| Avena sativa | Oats |
| Secale cereale | Rye |
| Zea mays | Maize |
| Spinacia oleracea | Spinach |
| Vicia faba | Horse bean |
| Trifolium pratense | Purple clover |
| Beta vulgaris | Sugar beet |
| Raphanus sativus var.radicula | Radish |
| Cucumis sativa | Cucumber |
| Phelum pratense | Timothy | were sprayed with the emulsion, described in Example 8, of the compounds according to the invention. At the time of treatment, the varieties of cereal and maize had formed 3 leaves, the timothy was in the tillering stage and the sugar beets, horse beans, radishes, spinach and cucumbers had formed the cotyledons or primary leaves and the first pair of foliage leaves. Purple clover was treated after the first trifoliate leaf had developed.

The dosage corresponded to 0.6 and 1.2 kg of active substance per hectare.

14 Days after the treatment, the degree of damage to the crop plants was determined in accordance with the following scheme:

| Rating of damage to the crop plants | Corresponding to % thinning-out or scorching or inhibition of growth |
|---|---|
| 1 | 0 |
| 2 | 2.5 |
| 3 | 5 |
| 4 | 10 |
| 5 | 15 |
| 6 | 25 |
| 7 | 35 |
| 8 | 67.5 |
| 9 | 100 |

Example 9

| Formula I R = | Hal. | Active compound f kg/ha | | Toleration by crop plants (ratings 1 - 9) | | | | | | | | | | | |
|---|---|---|---|---|---|---|---|---|---|---|---|---|---|---|---|
| | | | | Trit. vulg. | Hord. sat. | Avena sat. | Secale cor. | Zea mays | Spin. oler. | Vic. f. | Trif. prat. | Beta vulg. | Raph. sat. | Cuc. sat. | Ph. prat. |
| C$_2$H$_5$ | Cl | 0.6 | 1.2 | 1/1 | 1/1 | 1/1 | 1/1 | 1/1 | 6/7 | 2/2 | 3/4 | 9/9 | 3/3 | 3/3 | 2/2 |
| C$_3$H$_7$ | Cl | | | 1/1 | 1/1 | 1/1 | 1/1 | 1/1 | 8/9 | 2/3 | 2/2 | 9/9 | 2/2 | 3/3 | 1/2 |
| CH.(CH$_3$)$_2$ | Cl | | | 1/1 | 1/1 | 1/1 | 1/1 | 1/1 | 5/7 | 3/4 | 6/7 | 9/9 | 7/8 | 5/6 | 2/2 |
| C$_4$H$_9$ | Cl | | | 1/1 | 1/1 | 1/1 | 1/1 | 1/1 | 3/3 | 2/2 | 2/2 | 9/9 | 1/2 | 2/2 | 1/1 |
| CH$_2$CH.(CH$_3$)$_2$ | Cl | | | 1/1 | 1/1 | 1/1 | 1/1 | 1/1 | 5/7 | 3/3 | 3/4 | 9/9 | 3/4 | 2/2 | 1/2 |
| C$_7$H$_{15}$ | Cl | | | 1/1 | 1/1 | 1/1 | 1/1 | 1/1 | 5/7 | 2/3 | 6/7 | 9/9 | 3/3 | 2/3 | 1/1 |
| CH.(C$_2$H$_5$).C$_4$H$_9$ | Cl | | | 1/1 | 1/1 | 1/1 | 1/1 | 1/1 | 4/6 | 2/2 | 6/6 | 9/9 | 3/4 | 2/2 | 1/2 |
| C$_6$H$_{13}$ | Cl | | | 1/1 | 1/1 | 1/1 | 1/1 | 1/1 | 9/9 | 4/4 | 8/8 | 9/9 | 5/5 | 3/3 | 1/2 |
| C$_8$H$_{17}$ | Cl | | | 1/1 | 1/1 | 1/1 | 1/1 | 1/1 | 8/9 | 5/6 | 8/9 | 9/9 | 8/8 | 3/4 | 1/2 |
| C$_{13}$H$_{27}$ | Cl | | | 1/1 | 1/1 | 1/1 | 1/1 | 1/1 | 8/8 | 6/7 | 8/9 | 9/9 | 5/6 | 6/7 | 1/2 |
| C$_{17}$H$_{35}$ | Cl | | | 1/1 | 1/1 | 1/1 | 1/1 | 1/1 | 6/7 | 3/3 | 6/6 | 9/9 | 3/6 | 3/3 | 1/2 |
| O.C$_2$H$_5$ | Cl | 0.6 | 1.2 | 1/1 | 1/1 | 1/1 | 1/1 | 1/1 | 6/8 | 3/4 | 6/6 | 9/9 | 3/6 | 5/5 | 1/2 |
| O.CH.(CH$_3$)$_2$ | Cl | | | 1/1 | 1/1 | 1/2 | 1/1 | 1/1 | 7/9 | 4/6 | 7/8 | 9/9 | 3/6 | 5/5 | 1/2 |
| O.C$_4$H$_9$ | Cl | | | 1/1 | 1/1 | 1/2 | 1/1 | 1/1 | 7/9 | 4/6 | 7/8 | 9/9 | 3/6 | 4/5 | 1/2 |
| O.CH$_2$CH(CH$_3$)$_2$ | Cl | | | 1/1 | 1/1 | 1/1 | 1/1 | 1/1 | 6/6 | 3/3 | 6/6 | 9/9 | 3/6 | 2/2 | 1/2 |
| O.C$_5$H$_{11}$ | Cl | | | 1/1 | 1/1 | 1/2 | 1/1 | 1/1 | 7/9 | 6/8 | 8/8 | 9/9 | 3/8 | 5/5 | 1/2 |
| O.C$_6$H$_{13}$ | Cl | | | 1/1 | 1/1 | 1/1 | 1/1 | 1/1 | 6/6 | 3/3 | 6/6 | 9/9 | 3/3 | 3/4 | 1/2 |
| O.C$_7$H$_{15}$ | Cl | | | 1/1 | 1/1 | 1/2 | 1/1 | 1/1 | 9/9 | 6/8 | 7/8 | 9/9 | 3/3 | 5/5 | 1/2 |
| O.C$_8$H$_{17}$ | Cl | | | 1/1 | 1/1 | 1/2 | 1/1 | 1/1 | 8/8 | 6/6 | 7/8 | 9/9 | 3/6 | 3/4 | 1/2 |
| O.CH$_2$CH(C$_2$H$_5$)C$_4$H$_9$ | Cl | | | 1/1 | 1/1 | 1/1 | 1/1 | 1/1 | 7/8 | 6/8 | 5/5 | 9/9 | 3/6 | 2/4 | 1/2 |
| O.C$_{10}$H$_{21}$ | Cl | | | 1/1 | 1/1 | 1/1 | 1/1 | 1/1 | 9/9 | 8/9 | 6/8 | 9/9 | 8/8 | 3/4 | 1/2 |
| C(CH$_3$)$_3$ | Cl | | | 1/1 | 1/1 | 1/2 | 1/1 | 1/1 | 8/8 | 6/8 | 8/8 | 9/9 | 6/6 | 3/3 | 1/2 |
| O.CH$_2$CH$_2$CH(CH$_3$)$_2$ | Cl | | | 1/1 | 1/1 | 1/1 | 1/1 | 1/1 | 8/8 | 6/8 | 8/8 | 9/9 | 6/6 | 4/6 | 1/2 |
| C$_3$H$_7$ | Br | | | 1/1 | 1/1 | 1/2 | 1/1 | 1/1 | 7/8 | 6/8 | 6/8 | 8/9 | 5/6 | 4/5 | 2/2 |
| C$_7$H$_{15}$ | Br | | | 1/1 | 1/1 | 1/2 | 1/1 | 1/1 | 8/8 | 7/8 | 8/8 | 7/8 | 4/5 | 5/5 | 1/2 |
| O.C$_5$H$_{11}$ | Br | | | 1/1 | 1/1 | 1/2 | 1/1 | 1/1 | 8/9 | 7/8 | 8/8 | 8/9 | 5/6 | 4/4 | 1/2 |

As can be seen from Example 8, the use of the compounds according to the invention leads to 100% success in combating a series of weeds even when using amounts of only between 380 and 1,160 g of the active compound per hectare.

Example 9 shows that in the case of a number of crop plants there is good to very good toleration of the compounds listed. The group of the grasses, in particular, proved to be largely tolerant so that the compounds can be used for combating weeds, for example in cereal cultures.

What we claim is:

1. A phenylpyridazine having the formula

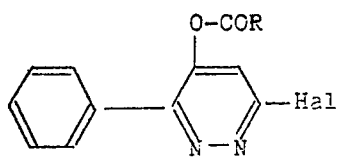

in which Hal is an atom selected from the group consisting of chlorine and bromine and R is selected from the group consisting of straight-chain or branched alkyl having 2 to 20 carbon atoms, when Hal is chlorine, and, when Hal is bromine, having 1 to 20 carbon atoms, and consisting of the group OR', wherein R' is selected from the group consisting of straight-chain or branched alkyl having 1 to 18 carbon atoms.

2. The phenylpyridazine according to claim 1 3-Phenyl-6-chloro-pyridazinyl-(4)-propionic acid ester.

3. The phenylpyridazine according to claim 1 3-Phenyl-6-chloro-pyridazinyl-(4)-n-butyric acid ester.

4. The phenylpyridazine according to claim 1 3-Phenyl-6-chloro-pyridazinyl-(4)-iso-butyric acid ester.

5. The phenylpyridazine according to claim 1 3-Phenyl-6-chloro-pyridazinyl-(4)-n-valeric acid ester.

6. The phenylpyridazine according to claim 1 3-Phenyl-6-chloro-pyridazinyl-(4)-iso-valeric acid ester.

7. The phenylpyridazine according to claim 1 3-Phenyl-6-chloro-pyridazinyl-(4)-2'-ethylhexanoic acid ester.

8. The phenylpyridazine according to claim 1 3-Phenyl-6-chloro-pyridazinyl-(4)-caprylic acid ester.

9. The phenylpyridazine according to claim 1 3-Phenyl-6-chloro-pyridazinyl-(4)-stearic acid ester.

10. The phenylpyridazine according to claim 1 3-Phenyl-6-chloro-pyridazinyl-(4)-pivalic acid ester.

11. The phenylpyridazine according to claim 1 3-Phenyl-6-chloro-pyridazinyl-(4)-caproic acid ester.

12. The phenylpyridazine according to claim 1 3-Phenyl-6-chloro-pyridazinyl-(4)-oenanthic acid ester.

13. The phenylpyridazine according to claim 1 3-Phenyl-6-chloro-pyridazinyl-(4)-pelargonic acid ester.

14. The phenylpyridazine according to claim 1 3-Phenyl-6-chloro-pyridazinyl-(4)-myristic acid ester.

15. The phenylpyridazine according to claim 1 3-Phenyl-6-chloro-pyridazinyl-(4)-n-pentyl-carbonate.

16. The phenylpyridazine according to claim 1 3-Phenyl-6-chloro-pyridazinyl-(4)-ethyl carbonate.

17. The phenylpyridazine according to claim 1 3-Phenyl-6-chloro-pyridazinyl-(4)-isopropyl carbonate.

18. The phenylpyridazine according to claim 1 3-Phenyl-6-chloro-pyridazinyl-(4)-isobutyl carbonate.

19. The phenylpyridazine according to claim 1 3-Phenyl-6-chloro-pyridazinyl-(4)-n-hexyl carbonate.

20. The phenylpyridazine according to claim 1 3-Phenyl-6-chloro-pyridazinyl-(4)-2-ethylhexyl carbonate.

21. The phenylpyridazine according to claim 1 3-Phenyl-6-chloro-pyridazinyl-(4)-n-propyl carbonate.

22. The phenylpyridazine according to claim 1 3-Phenyl-6-chloro-pyridazinyl-(4)-n-butyl carbonate.

23. The phenylpyridazine according to claim 1 3-Phenyl-6-chloro-pyridazinyl-(4)-isoamyl carbonate.

24. The phenylpyridazine according to claim 1 3-Phenyl-6-chloro-pyridazinyl-(4)-n-heptyl carbonate.

25. The phenylpyridazine according to claim 1 3-Phenyl-6-chloro-pyridazinyl-(4)-n-octyl carbonate.

26. The phenylpyridazine according to claim 1 3-Phenyl-6-chloro-pyridazinyl-(4)-n-decyl carbonate.

27. The phenylpyridazine according to claim 1 3-Phenyl-6-bromo-pyridazinyl-(4)-n-butyric acid ester.

28. The phenylpyridazine according to claim 1 3-Phenyl-6-bromo-pyridazinyl-(4)-n-octanoic acid ester.

29. The phenylpyridazine according to claim 1 3-Phenyl-6-bromo-pyridazinyl-(4)-n-amyl carbonate.

30. The phenylpyridazine according to claim 1, having the formula

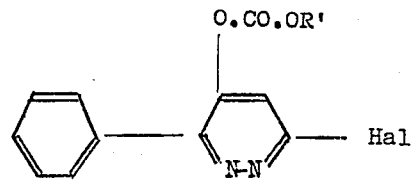

wherein R' is alkyl having 1 to 18 carbon atoms and Hal is selected from the group consisting of chlorine and bromine.

* * * * *